(12) United States Patent
Pell

(10) Patent No.: US 6,782,075 B2
(45) Date of Patent: Aug. 24, 2004

(54) METHOD OF MAKING <200 NM WAVELENGTH FLUORIDE CRYSTAL LITHOGRAPHY/LASER OPTICAL ELEMENTS

(75) Inventor: Michael A. Pell, Fountainebleau (FR)

(73) Assignee: Corning Incorporated, Corning, NY (US)

( * ) Notice: Subject to any disclaimer, the term of this patent is extended or adjusted under 35 U.S.C. 154(b) by 102 days.

(21) Appl. No.: 10/228,969

(22) Filed: Aug. 26, 2002

(65) Prior Publication Data

US 2003/0048872 A1 Mar. 13, 2003

(30) Foreign Application Priority Data

Aug. 27, 2001 (FR) ............................................. 01 11144

(51) Int. Cl.[7] .......................................... G01N 23/207
(52) U.S. Cl. ............................. 378/73; 378/71; 378/72; 378/75
(58) Field of Search ............................... 378/71, 72, 73, 378/74, 75, 76

(56) References Cited

U.S. PATENT DOCUMENTS

| | | | | |
|---|---|---|---|---|
| 5,442,676 A | * | 8/1995 | Fewster | 378/72 |
| 6,385,289 B1 | * | 5/2002 | Kikuchi | 378/79 |
| 6,389,100 B1 | * | 5/2002 | Verman et al. | 378/84 |
| 6,395,657 B2 | * | 5/2002 | Mayolet et al. | 501/3 |
| 6,498,829 B1 | * | 12/2002 | Borgstahl et al. | 378/73 |

OTHER PUBLICATIONS

B. D. Cullity. Elements of X–Ray Diffraction, second edition (Reading, MA: Addison–Wesley, 1978), p. 103, 104, 277, 278.*

* cited by examiner

Primary Examiner—Edward J. Glick
Assistant Examiner—Allen C. Ho
(74) Attorney, Agent, or Firm—Walter M. Douglas

(57) ABSTRACT

The invention provides for the making of <200 nm wavelength fluoride crystal optical elements from selected fluoride single crystals of determined quality.

The invention relates to a method of determining the optical quality of a fluoride single crystal.

The method according to the invention is characterised in that it comprises the following steps:

(a) irradiating at least one volume element of the fluoride single crystal, along at least one given family of crystalline planes with a hard X-ray beam, in order to obtain a picture of the diffraction in transmission mode of the hard X-rays across this at least one volume element along this at least one family of crystalline planes, (b) studying the picture obtained in step (a), and (c) calculating the mosaicity of the at least one volume element along the at least one family of crystalline planes, from the study of step (b).

The invention finds application in the field of the optical industry.

9 Claims, 5 Drawing Sheets

METHOD OF MAKING <200 NM WAVELENGTH FLUORIDE CRYSTAL LITHOGRAPHY/LASER OPTICAL ELEMENTS

BACKGROUND OF THE INVENTION

Field of the Invention

The invention relates to a method of determining the optical quality of a fluoride single crystal, and the making of <200 nm lithography laser optical elements.

There currently exists a strong demand for optical lithography exposure tools which function at 193 and 157 nm excimer laser wavelengths.

In this regard, optical fluoride crystals are used as optical elements in illumination systems, projections systems and excimer lasers, due to their transmission and durability which make them optical materials which are ideal for applications at wavelengths of less than 200 nm.

This region of the electromagnetic spectrum is of great interest, in particular for high resolution microlithography systems.

A microlithography system contains sub-systems which are mainly the illumination system and the projection system.

The projection system is for focalising the picture and therefore the optical elements which include it must be of a superior optical quality.

In this respect, the optical homogeneity of the crystals must be less than 2 ppm, and preferably less than 1 ppm, for applications in projection systems.

As for the illumination system, this is for forming the laser beam and the requirements upon the crystalline quality of the optical elements which include it are also very high, although lower than for the projection system.

Up to now, the quality of the single crystals constituting such optical elements was optically checked by measuring the birefringence, the optical homogeneity, and by a general visual inspection of the single crystals. However, these techniques only offer an optical macroscopic view of the quality of the crystal. The commercial use and adoption of 193 nm and below 200 nm vacuum ultraviolet wavelengths such as 157 nm has been hindered by the transmission nature of such deep ultraviolet wavelengths in the 157 nm region through optical materials. Such slow progression by the semiconductor industry of the use of VUV light below 200 nm such as the 157 nm region light has been also due to the lack of economically manufacturable blanks from optically transmissive materials and difficulties in manufacturing blanks which can be identified as high quality and qualified for their intended microlithography optical element and laser use. For the benefit of below 200 nm deep ultraviolet photolithography in the VUV 157 nm region such as the emission spectrum of the fluorine excimer laser to be utilized in the manufacturing of integrated circuits there is a need for below 200 nm wavelength transmitting optical fluoride crystals that have beneficial optical and highly qualified properties including good transmission below 200 nm and at 193 nm and 157 nm and that can be manufactured reliably and economically. The present invention overcomes problems in the prior art and provides a means for economically providing high quality below 200 nm wavelength transmitting optical fluoride crystals, element blanks, and elements that can be used to improve the manufacturing of integrated circuits with vacuum ultraviolet wavelengths. The invention provides for determination and selection of high quality calcium fluoride optical fluoride crystal lithography and excimer laser elements with low mosaicity levels.

SUMMARY OF THE INVENTION

Figure 1:
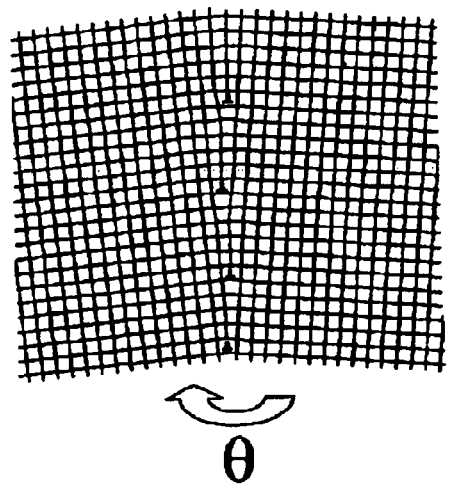
FIG. 1 represents a schematic view of a dislocation at a grain boundary in a single crystal.

Now, it has been seen for applications in high resolution projection systems that the optical homogeneity of the crystals must be less than 2 ppm, and preferably less than 1 ppm, which signifies that the checking of the optical quality of the crystal must be effected microscopically, in contrast to macroscopically, which the currently used methods do not use.

The invention aims to alleviate the drawbacks of the prior art methods of determination of the optical quality of a single crystal, in particular of a fluoride single crystal, by proposing a method which enables the micro-defects in these single crystals to be detected.

This method of making <200 nm wavelength optical elements is based on X-ray volume analysis of the single optical fluoride crystal.

Thus, the invention proposes a method of determining the optical quality of a fluoride single crystal for fitness for making into an optical element, characterised in that it comprises steps of (a) irradiating at least one volume element of the fluoride single crystal, along at least one family of crystalline planes with a hard X-ray beam, in order to obtain a picture of the diffraction in transmission mode of the hard X-rays across this at least one volume element along this at least one family of crystalline planes, (b) studying the picture obtained in step (a), and (c) calculating the mosaicity of the at least one volume element along the at least one family of crystalline planes, from the study of step (b).

Preferably, steps (a) to (c) are repeated along several families of crystalline planes in the at least one volume element.

Advantageously, steps (a) to (c) are repeated in several different elements of volume of the fluoride single crystal.

In these latter cases, the total mosaicity of the fluoride single crystal is calculated from the mosaicity calculations obtained in steps (c).

The volume element has a thickness, in the direction of the thickness of the optical fluoride single crystal, of 3 to 10 cm, and a surface area irradiated by the hard X-ray beam of 0.5 mm×20 to 40 mm.

The invention includes making a below 200 nm wavelength fluoride crystal optical element. In accordance with the invention the method includes providing a fluoride single crystal, irradiating at least one volume element of the fluoride single crystal, along at least one family of crystalline planes with a hard x-ray beam, in order to obtain a picture of the diffraction in transmission mode of the hard x-rays across this at least one volume element along this at least one family of crystalline planes, studying the picture of the diffraction in transmission mode and calculating a mosaicity of the at least one volume element along the at least one family of crystalline planes to provide a selected optical fluoride crystal blank having a determined mosaicity of less than 10' across the at least one volume element, and forming said selected optical fluoride crystal having a determined mosaicity of less than 10' across the at least one volume element into a below 200 nm wavelength fluoride crystal optical element having a mosaicity of less than 10'.

The invention includes making a below 200 nm wavelength fluoride crystal optical lithography projection element blank for forming into a below 200 nm wavelength fluoride crystal optical lithography projection element. In accordance with the invention the method includes providing a fluoride single crystal, irradiating at least one volume element of the fluoride single crystal, along at least one family of crystalline planes with a hard x-ray beam, in order to obtain a picture of the diffraction in transmission mode of the hard x-rays across this at least one volume element along this at least one family of crystalline planes, studying the picture of the diffraction in transmission mode and calculating a mosaicity of the at least one volume element along the at least one family of crystalline planes to provide a selected below 200 nm wavelength fluoride crystal optical lithography projection element crystal blank having a determined mosaicity of less than 10' across the at least one volume element. The invention includes a below 200 nm wavelength fluoride crystal optical lithography projection element blank for forming into a below 200 nm wavelength fluoride crystal optical lithography element, said blank comprised of an x-ray beam irradiated optical fluoride single crystal having a determined mosaicity of less than 10' across an at least one volume element of said fluoride single crystal, along at least one family of crystalline planes.

Preferably, the optical fluoride single crystals are selected for making into a <200 nm optical element with the selected crystal having a mosaicity of less than 10' across the given at least one volume element.

The method of the invention is of a particular interest for the fluoride single crystals which are or can be used in the projection systems, such as the single crystals of NaF, of KF, of LiF, of $CaF_2$, of $BaF_2$, of $MgF_2$, or of $SrF_2$, or the mixed combinations of the latter fluorides, such as, for example, combinations of formulation $(M1)_x(M2)_{1-x}F_2$ in which M1 can be selected from Ba, Ca or Sr and x is such that $0 \leq x \leq 1$, or even combinations of formulation $Ca_{1-x-y}Ba_xSr_yF_2$ in which x and y are such that $0 \leq x \leq 1$ and $0 \leq y \leq 1$, or even combinations of formulation $MRF_3$ in which M can be selected from Li, Na or K, and R can be selected from Ca, Sr, Ba or Mg.

The invention also proposes an <200 nm wavelength fluoride crystal projection lithography optical element for use in projection systems which function at wavelengths of between 100 and 200 nm, characterised in that it is constituted of a fluoride single crystal having a mosaicity of less than 10'.

Preferably, the fluoride single crystal is a single crystal of NaF, of KF, of LiF, of $CaF_2$, of $BaF_2$, of $MgF_2$, or of $SrF_2$, or the mixed combinations of the latter fluorides, such as, for example, combinations of formulation $(M1)_x(M2)_{1-x}F_2$ in which M1 can be selected from Ba, Ca or Sr and x is such that $0 \leq x \leq 1$, or even combinations of formulation $Ca_{1-x-y}Ba_xSr_yF_2$ in which x and y are such that $0 \leq x \leq 1$ and $0 \leq y \leq 1$, or even combinations of formulation $MRF_3$ in which M can be selected from Li, Na or K, and R can be selected from Ca, Sr, Ba or Mg.

In the case of the mixed single crystals, the variables x and y are selected in order to obtain the particular properties sought after for a particular application. For example, the variables x and y can be selected such that the characteristics of dispersion of the single crystal are optimal, and for applications, so as to minimise the intrinsic birefringence of the single crystal along a given crystallographic direction, and at a given wavelength below 200 nm.

The invention will be better understood and other advantages and features will appear more clearly upon reading the explanatory description which follows and which is made with reference to the annexed Figures.

DETAILED DESCRIPTION OF THE INVENTION

The optical quality of a single crystal is strongly affected by the presence of microscopic defects in its crystalline structure.

A single crystal is in fact constituted of a large number of sub-grains with the limits between themselves being defined by what is called sub-grain boundaries.

It is about these sub-grain boundaries that most of the defects appear which have a negative influence upon the optical quality of the single crystal and particularly upon the optical homogeneity of the single crystal.

Now, the optical homogeneity of the single crystal is an important factor for its use in high resolution optical systems.

The optical homogeneity is a measure of the optical quality of a single crystal. It is representative of the difference between the optical indices found in each region of the single crystal.

A defect which affects the optical quality of a single crystal is the presence of dislocations at the boundaries of sub-grains in the single crystal represented.

FIG. 1 represent an entirety of dislocations at a boundary between two sub-grains of a single crystal.

As is seen in FIG. 1, the two sub-grains form an angle marked θ in FIG. 1, about the boundary of sub-grains separating them. This change in orientation of a sub-grain with respect to another is due to microscopic dislocations. These dislocations manifest themselves by a local change in the density and in the polarizability of the single crystal. Thus, at this boundary, there is a local change in the refractive index of the single crystal.

Moreover, the more the angle θ between two sub-grains increases, the higher the disorientation of the sub-grains is.

Now, when the disorientation of a sub-grain in the crystal increases with respect to the sub-grains which are the nearest to it, the sub-grain passes from the state which is known as a "sub-grain" to the "grain" state.

There are no strict rules for quantifying this boundary, but it is recognised that if the angle θ increases, the entire single crystal no longer behaves as a single crystalline material but as a polycrystalline material.

Figure 2:
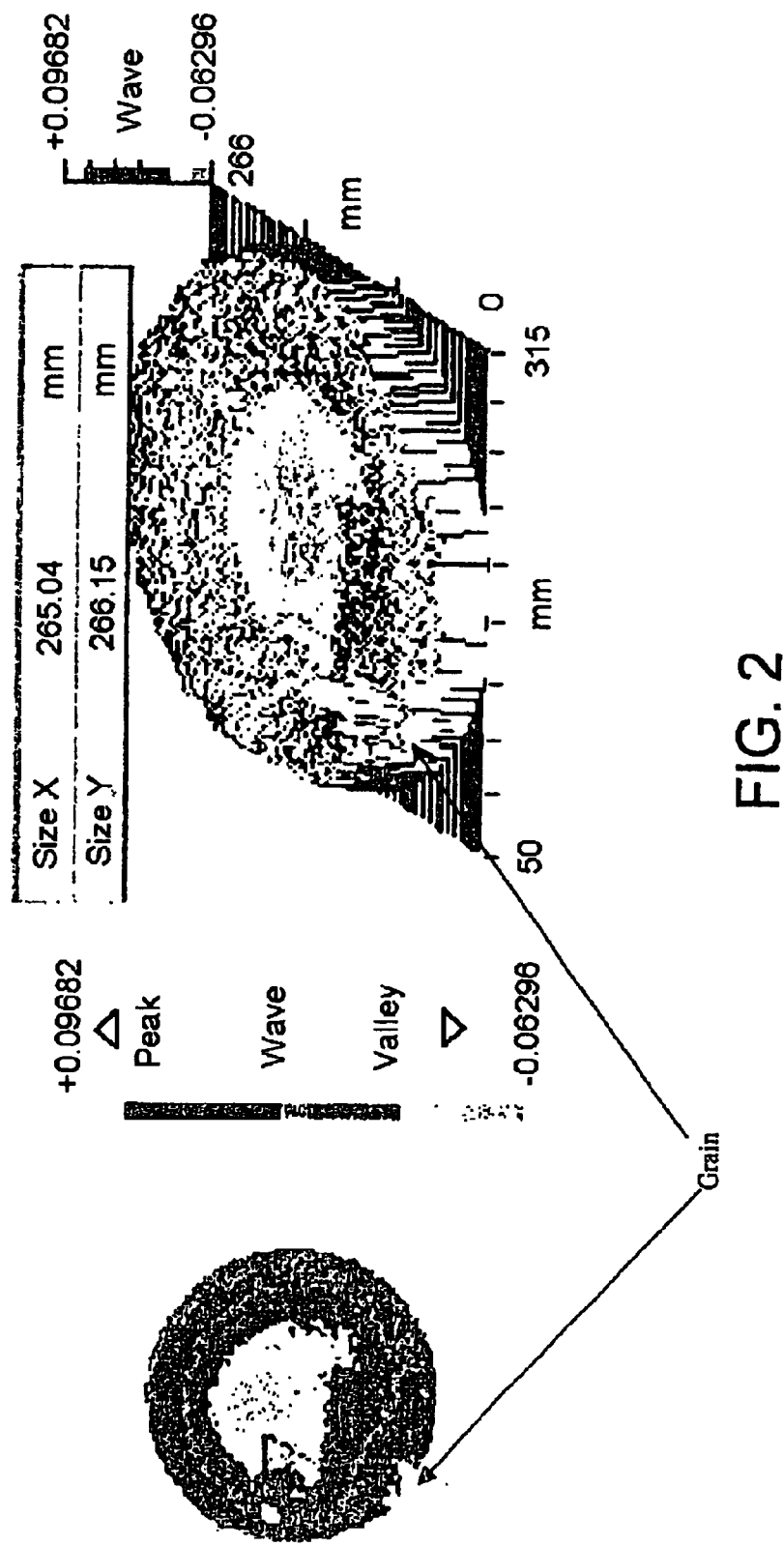
FIG. 2 represents the results of the measurements of the optical homogeneity of a sample of $CaF_2$ having a plurality of sub-grains, which is measured by using an interferometer.

This can be visualised in FIG. 2 which shows two pictures of the results of the measurements of the optical homogeneity of a sample of single crystal of $CaF_2$, this measurement having been made by using an interferometer, and which represent the optical homogeneity of a single crystal of $CaF_2$ which has a plurality of sub-grains around its circumference.

In the sample of $CaF_2$, represented in FIG. 2, one of the sub-grains of the circumference possesses such a disorientation with respect to the sub-grains which are the nearest to it, that it forms a prominent grain as detected in accordance with the invention.

This grain is indicated by the arrows in FIG. 2.

The presence of this grain leads to the fact that the value of the optical homogeneity of this sample of $CaF_2$ is higher, i.e. that the optical homogeneity of the sample in its entirety is not as good, the effect of the disorientation being particularly dramatic upon the optical homogeneity in the region of the prominent grain.

Thus, the macroscopic optical quality of a fluoride single crystal such as observed with an interferometer depends strongly upon the "microscopic" crystalline defects of this single crystal.

The term "microscopic" is understood as meaning in the invention defects ranging from a nanometer to a micron.

Now, up to present, the optical homogeneity and thus the optical quality of a fluoride single crystal was determined macroscopically and optically such as with an optical interferometer.

In accordance with the invention, an ideal method for observing the microscopic defects in <200 nm wavelength optical fluoride crystals is to use a volume analyses method by irradiation of the crystals by hard X-rays.

This method implies the positioning of the sample between a detector and a source of hard X-rays with an energy of higher than 100 ke V and a band length $\Delta\lambda$ with an angular opening $\Delta\theta$.

The sample is orientated in the hard X-rays beam in order to observe the diffraction of a given family of crystalline planes.

The effective size of the beam on the surface of the sample can be high, but preferably the size of the beam on the surface of the sample will be regulated such that it sweeps over a surface of the sample of 0.5 mm by about 2 to 4 cm.

By this technique, pieces of information on a significant volume element, the optical quality of which it is desired to determine, are obtained.

As the measurement takes only a few seconds, it is possible to rapidly make numerous measurements across the sample in order to thus obtain a complete picture of the structure of the defects of the crystal.

It is possible to work in transmission mode and from then on to obtain pieces of information, notably on the crystalline defects, over the entire thickness of the crystal.

This is possible by virtue of the significant intensity of the X-ray source and by virtue of the very low absorption of the fluoride crystals at these wavelengths.

It is here where the advantageous effect resides, in particular of the method of the invention.

It is thus possible to determine, with high reliability, the optical quality of the crystal and thus its suitability as an optical element for devices functioning between 100 and 200 nanometers.

It is so that it has been discovered that it was possible to measure the optical quality of a volume element over the entire thickness of crystals having a thickness, which can exceed 10 cm. and its fitness for making into a <200 nm optical element.

However, for an application as an optical element in high resolution systems, such as projection systems, the thickness of the single crystals used is generally between 3 and 10 cm, and this renders the method of the invention entirely suitable.

The method makes use of a hard X-ray diffractometer.

It provides a direct measurement of the mosaicity of the crystal, also called the "mosaic spread".

The mosaicity is a measurement of the optical quality of the crystal.

More precisely, the mosaicity reflects the relative orientation of the grains and sub-grains of the crystal in a given volume element.

The beam diffracted by each grain or sub-grain is in fact recorded on the detector at a position linked to the orientation of this grain or sub-grain with respect to the neighbouring grains or sub-grains. This relative orientation is calculated directly on the projected picture.

Now, it has been seen when the disorientation of a sub-grain with respect to its nearest neighbours increases, the homogeneity and the optical quality of the crystal are not as good.

Thus, in a first aspect, the invention proposes a method of determining the optical quality of a single crystal for fitness in making into <200 nm wavelength optical lithography element, preferably a fluoride single crystal, which comprises an irradiating at least one volume element of the single crystal, along at least one given family of crystalline planes with a hard X-ray beam, in order to obtain a picture of the diffraction in transmission mode of the hard X-rays across this at least one volume element and along this at least one family of crystalline planes.

With the aid of this single operation, the calculation of the mosaicity of this volume element along this family of crystalline planes is made by studying the picture obtained, and this enables the optical quality of the single crystal and fitness for making into an optical element to be determined.

Since each one of these measurements being made along a family of crystalline planes in the particular volume element of the fluoride single crystal taking a few seconds, it is particularly advantageous not only to repeat this measurement along several families of crystalline planes in the at least one particular volume element, but also to repeat it in several different volume elements of the fluoride single crystal.

In the two cases, the calculation of the total mosaicity of the fluoride single crystal is done, obviously, from mosaicity values obtained in each measurement.

With the method of the invention, it is possible to regulate the size of the hard X-ray beam by brushing over the single crystal such that the given volume element have a thickness, in the direction of the thickness of the fluoride single crystal, of 3 to 10 cm, and a surface area irradiated by the hard X-ray beam of about 0.5 mm×20 to 40 mm.

Figure 7:
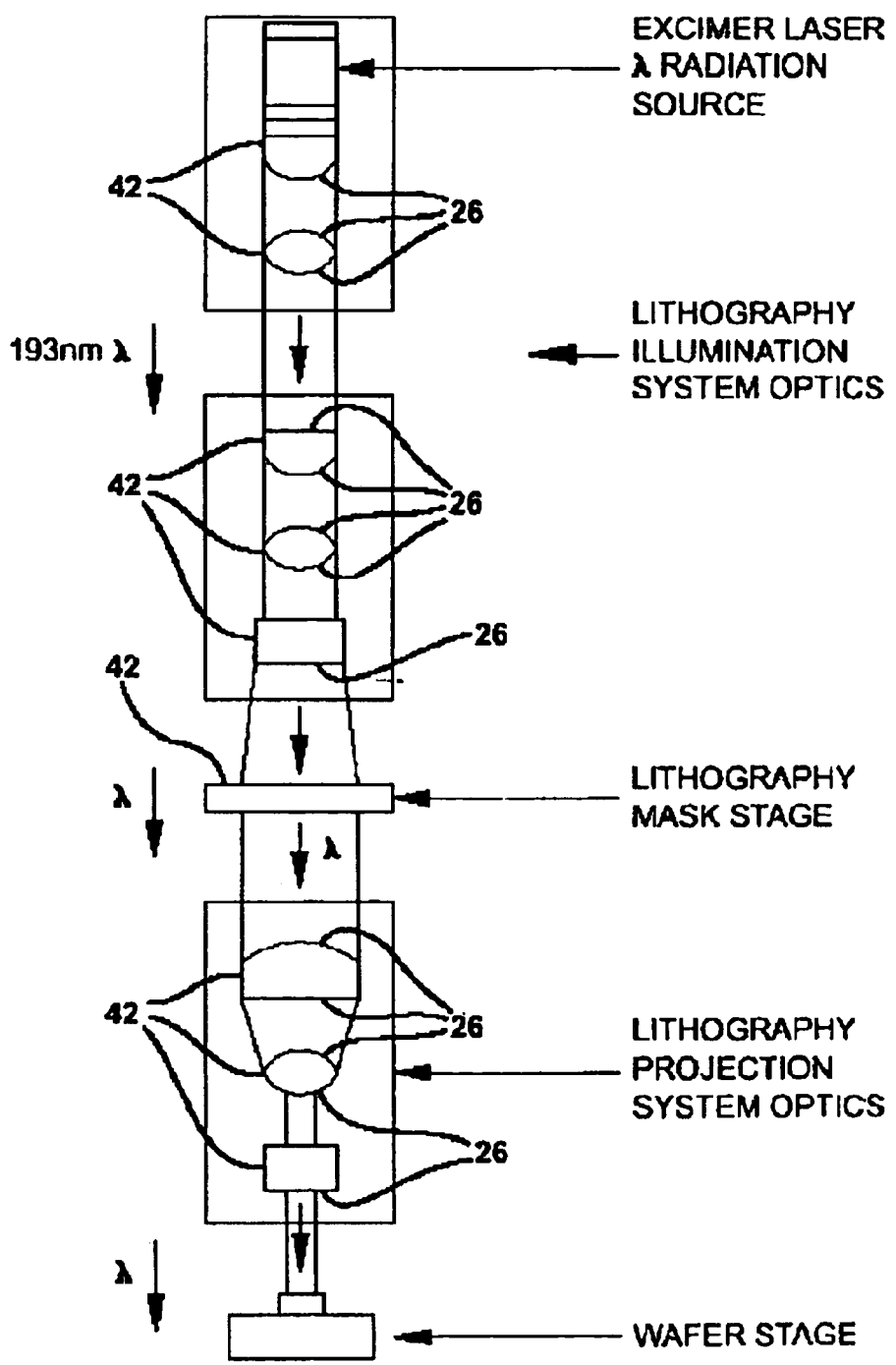
FIG. 7 shows an embodiment of the invention.

FIG. 7 shows a below 200 nm optical lithography system/method that operates at the 157 nm wavelength of a $F_2$ excimer laser with below 200 nm optical lithography fluoride crystal elements 42 in accordance with the invention.

Figure 8:
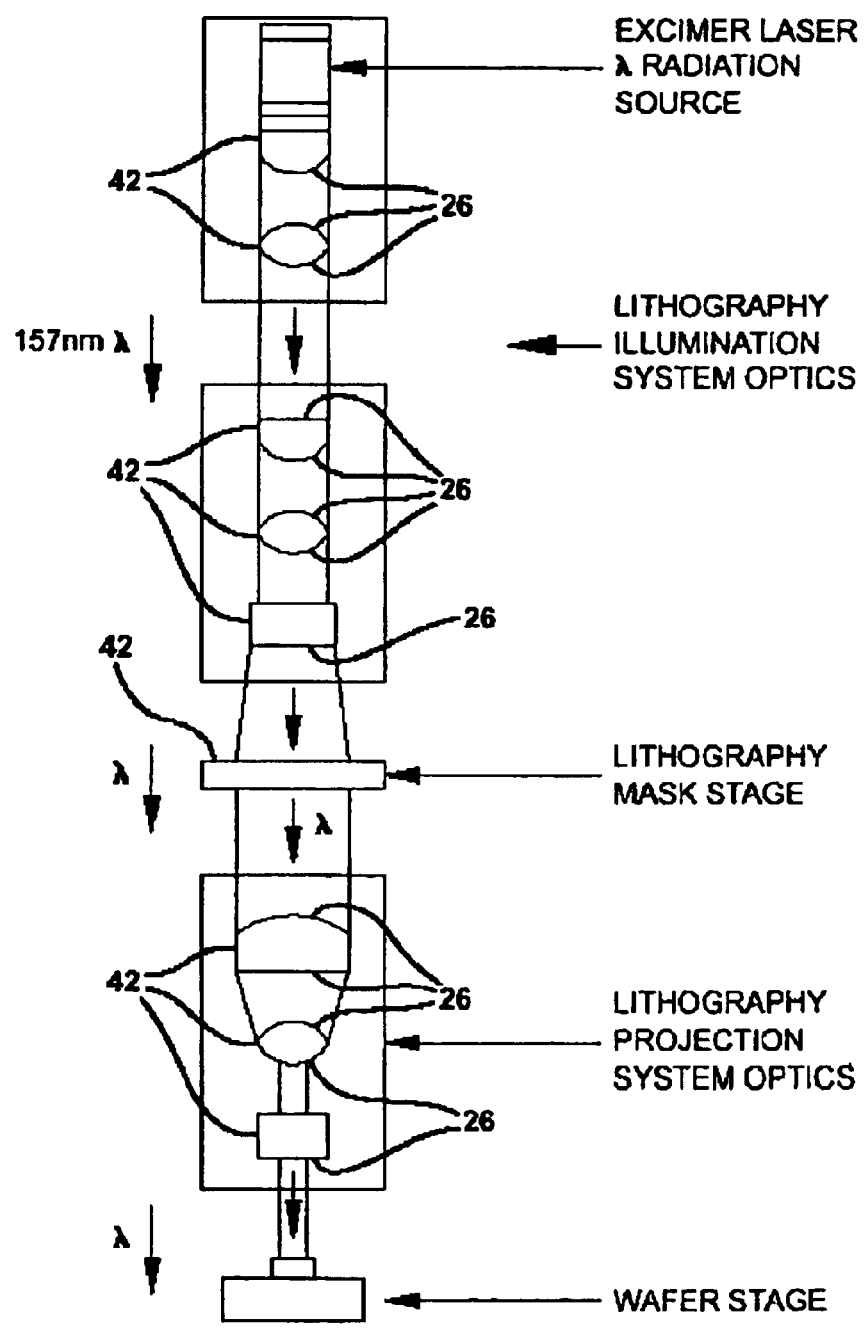
FIG. 8 shows an embodiment of the invention.

FIG. 8 shows a below 200 nm optical lithography system/method that operates at the 193 nm wavelength of an ArF excimer laser with below 200 nm optical lithography fluoride crystal elements 42 in accordance with the invention. Below 200 nm optical lithography fluoride crystal elements 42 are formed with finished polished shaped optical surfaces 26 for transmitting and operating on the below 200 nm lithography light.

Figure 9:
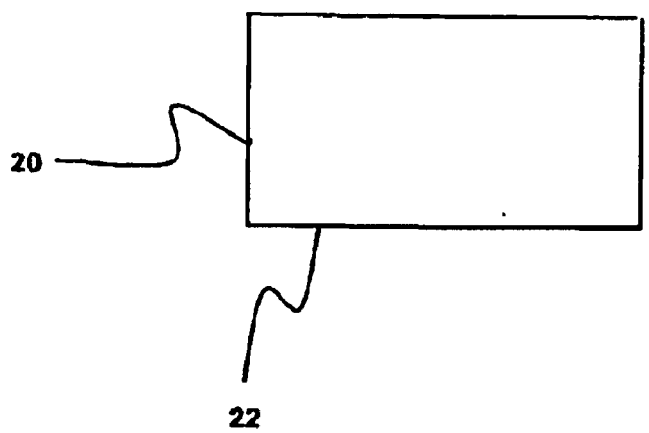
FIG. 9 shows an embodiment of the invention.
Figure 10:
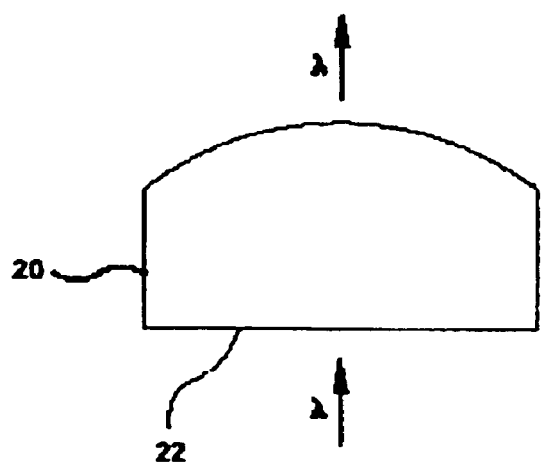
FIG. 10 shows an embodiment of the invention.

FIG. 9 shows a cross-section side view of a below 200 nm wavelength optical fluoride crystal disk. In accordance with the invention, the optical fluoride crystal 20 is irradiated with an x-ray beam to determine if the crystal has a mosaicity of less than 10' to determine if the crystal 20 can be selected to be a selected optical fluoride crystal blank having a determined mosaicity of less than 10' across an at least one volume element 22 for formation into a below 200 nm wavelength fluoride crystal optical element such as shown in FIG. 10 for use in below 200 nm optical lithography systems as an optical element 42, preferably as a projection element of the lithography projection system optics.

For a use as an optical element for devices functioning between 100 and 200 nm, fluoride single crystals are selected which have a mosaicity of less than 10' across the volume element.

The method of the invention applies in particular to the determination of the optical quality of a single crystal of NaF, of KF, of LiF, of $CaF_2$, of $BaF_2$, of $MgF_2$, or of $SrF_2$, or the mixed combinations of the latter fluorides, such as, for example, combinations of formulation $(M1)_x(M2)_{1-x}F_2$ in which M1 can be selected from Ba, Ca or Sr and x is such that $0 \leq x \leq 1$, or even combinations of formulation $Ca_{1-x-y}Ba_xSr_yF_2$ in which x and y are such that $0 \leq x \leq 1$ and $0 \leq y \leq 1$, or even combinations of formulation $MRF_3$ in which M can be selected from Li, Na or K, and R can be selected from Ca, Sr, Ba or Mg.

Thus, an optical element according to the invention, for use of wavelengths of between 100 and 200 nm, is constituted of a fluoride single crystal having a mosaicity of less than 10' across a given volume element, the mosaicity having preferably been determined with the method of the invention.

In this case, the given volume element has a surface area of 0.5 mm×20 mm and a thickness, in the direction of the thickness of the fluoride single crystal, of 3 to 10 cm.

An optical element which is particularly interesting is a single crystal of NaF, of KF, of LiF, of $CaF_2$, of $BaF_2$, of $MgF_2$, or of $SrF_2$, or the mixed combinations of the latter fluorides, such as, for example, combinations of formulation $(M1)_x(M2)_{1-x}F_2$ in which M1 can be selected from Ba, Ca or Sr and x is such that $0 \leq x \leq 1$, or even combinations of formulation $Ca_{1-x-y}Ba_xSr_yF_2$ in which x and y are such that $0 \leq x \leq 1$ and $0 \leq y \leq 1$, or even combinations of formulation $MRF_3$ in which M can be selected from Li, Na or K, and R can be selected from Ca, Sr, Ba or Mg.

In order to better understand the invention, description will now be made of it as purely illustrative and non-limiting examples of several implementation means.

EXAMPLE 1

In this Example, a first calcium fluoride single crystal is irradiated with a hard X-ray beam, along several families of crystalline planes and in different volume elements of the single crystal.

At each measurement, the surface area of the single crystal brushed over by the hard X-ray beam was of 0.5 mm×20 mm and the thickness of the single crystal crossed by the hard X-rays was of 4 cm.

Consequently, each volume element had a surface area of 0.5 mm×20 mm and a depth of 4 cm.

Figure 3:
FIG. 3 represents the picture obtained by the method of determination of the invention, on a first single crystal of $CaF_2$.

An picture, representative of those obtained by applying the method of the invention on each volume element along each family of crystalline planes of this first sample of calcium fluoride single crystal, is represented in FIG. 3.

In FIG. 3, the vertical axis corresponds to the measured height or thickness of the sample.

The width of the picture obtained, i.e. the size of the picture obtained along the horizontal axis, is proportional to the mosaicity of the single crystal along this family of particular crystalline planes, in this particular volume element.

It has already been stated, the picture represented in FIG. 3 is representative of those obtained on the different volume elements and along the different families of crystalline planes, on this sample of fluoride single crystal, by applying the method of determination of the invention.

It emerges from the whole of the pictures obtained that the total mosaicity of the fluoride single crystal tested in this Example is of less than 1'.

In order to verify that such a value of the total mosaicity of the single crystal gives rise to a very good optical quality of this single crystal, measurement was made of the optical homogeneity of this single crystal optically, in this particular case by using an interferometer.

It proved to be that the total optical homogeneity of this single crystal is of 1.3 ppm.

It is thus seen that the mosaicity gives rise to a certain value of the optical homogeneity and thus of the optical quality of the single crystal.

Stated otherwise, the smaller the width of the picture obtained by applying the method of the invention, the lower the value is of the optical homogeneity of the whole of the single crystal, and therefore the better its optical homogeneity is.

In conclusion, the sample measured here is of very good quality and can be used as an optical element for projection systems which require a very good optical quality.

EXAMPLE 2

A second calcium fluoride single crystal sample was treated by the method according to the invention and as described in Example 1, except that the thickness of the single crystal crossed over by the X-rays was 10 cm.

Figure 4:
FIG. 4 represents the picture obtained by the method of determination of the invention, on a second single crystal of $CaF_2$.

An picture representative of those obtained by applying the method of the invention is represented in FIG. 4.

As is seen in FIG. 4, the picture obtained has an enlargement along the horizontal axis.

More precisely, it is distinguished on the lower half of the picture that there is an abrupt disorientation between the adjacent sub-grains, in the lower part of the sample crossed by the hard X-rays, and this manifests itself by the presence of marks dispersed in the lower part of the picture.

Moreover, it is seen in FIG. 4 that for this lower part, the enlargement of the picture obtained by applying the method of the invention to the calcium fluoride single crystal sample is more significant than in the upper part of the picture.

The result of the analysis of this picture is that for the grain on the left in the lower part of FIG. 4, the mosaicity is of 2.5'.

As for the upper part of the picture, its enlargement along the horizontal axis gives rise to a mosaicity of the grains in the upper part of the single crystal of about 5'.

The analysis of the whole of the pictures obtained enabled determining that the total mosaicity of the calcium fluoride single crystal according to this second Example is greater than 20'.

Here again, in order to verify that such a value of the total mosaicity was representative of the total optical quality of the single crystal, the value of the optical homogeneity was determined of this mode of crystal by using an interferometer.

The value of optical homogeneity found was of 11.6 ppm.

Such a value of optical homogeneity does not enable the sample of Example 2 to be used as an optical element for high resolution projection systems which function at wavelengths of 100 and 200 nm.

In fact, from the results of the different tests done on different samples of calcium fluoride single crystals, it was found that the mosaicity across a volume element of 0.5 mm×40 mm×3 to 10 cm thickness, preferably across the whole of the volume elements, must be less than 10', in order that the single crystal can advantageously be used as an optical element for projection systems.

EXAMPLE 3

The method of the invention as described in Example 1 was implemented on a third calcium fluoride single crystal.

Figure 5:
FIG. 5 represents the picture obtained by the method of determination of the invention on a third single crystal of $CaF_2$.
Figure 5:

An picture representative of those obtained by the method of the invention is represented in FIG. 5.

FIG. 5 illustrates the picture which appears on the detector, for a family of given planes in a given volume element.

On this picture, several marks appear which originate from diverse crystalline planes: a mark at the centre was exploited since it is representative of the family of crystalline planes according to which it was desired to measure.

Stated otherwise, the mosaicity values were measured from the central mark only.

As is seen in FIG. 5, the central mark possesses a large enlargement along the horizontal axis.

However, this enlargement is about constant over all the thickness of 4 cm of the volume element studied, in contrast to the sample of Example 2, and this shows that there is no abrupt disorientation of sub-grains.

The mosaicity of this sample, when calculated from the whole of the pictures obtained by applying the method of the invention is of 16'.

One again, the optical homogeneity of this single crystal was measured by using an interferometer. It is 6.9 ppm.

Here again, the calcium fluoride single crystal studied cannot be used as an optical element for high resolution applications, the mosaicity being greater than 10'.

EXAMPLE 4

The method of the invention was applied on a fourth calcium fluoride single crystal sample according to the method described in Example 1.

Figure 6:
FIG. 6 represents the picture obtained by the method of determination of the invention on a fourth single crystal of $CaF_2$.

An picture representative of those obtained is represented in FIG. 6.

As seen in FIG. 6, the enlargement along the horizontal axis of the picture obtained is lower than the enlargements of the pictures obtained in Examples 2 and 3.

This enlargement of the pictures obtained along the horizontal axis gives rise to a mosaicity of 9'.

The optical homogeneity of this sample, when measured by using an interferometer is of 1.9 ppm.

This calcium fluoride single crystal can be used as an optical element for projection systems since its mosaicity is less than 10', and this manifests itself by an optical homogeneity of less than 2 ppm.

However, when an optical homogeneity of the order of 1 ppm is required by the manufacturer or the user of the system, it cannot be used.

In fact, although the mosaicity of the single crystal here be in the form of a low but discontinuous disorientation of the sub-grains across the various volume elements, this low disorientation can be a disadvantage.

The hard X-ray technique can easily be used of detecting disorientations of boundaries of sub-grains of the order of 0.5'.

The technique gives pieces of information not only on the total mosaicity but also as to the presence of strong local dislocations which would not appear if only an overall analysis was carried out.

Now, the mosaic structure in crystals can have a negative impact upon the optical homogeneity.

In particular, this technique enables revealing the crystals with a high mosaic distribution which manifests itself by a high disorientation between the adjacent sub-grains.

It is preferred that the disorientation angle of a sub-grain with respect to its nearest neighbours be as low as possible.

The hard X-rays technique procures additional pieces of information on the mosaicity of a crystal across a given volume element which brushes over the entire thickness of the crystal.

As has been already stated, from the different tests made, it was determined that the mosaicity across a given volume element, the thickness of which corresponds to the thickness of the entire crystal, i.e. 4 to 10 cm and the upper surface area of which is of 0.5 mm×40 mm, must be less than 10'; preferably less than 9', preferably less than 1', preferably less than 0.5.

Of course, the invention is in no way limited to the embodiments described and illustrated which have been given only as examples.

Thus, although the invention has been described in the Examples solely with reference to a calcium fluoride crystal, it will be possible for the method of the invention to be applied to other fluoride single crystals such as single crystals of NaF, of KF, of LiF, of $CaF_2$, of $BaF_2$, of $MgF_2$, or of $SrF_2$, or the mixed combinations of the latter fluorides, such as, for example, combinations of formulation $(M1)_x(M2)_{1-x}F_2$ in which M1 can be selected from Ba, Ca or Sr and x is such that $0 \leq x \leq 1$, or even combinations of formulation $Ca_{1-x-y}Ba_xSr_yF_2$ in which x and y are such that $0 \leq x \leq 1$ and $0 \leq y \leq 1$, or even combinations of formulation $MRF_3$ in which M can be selected from Li, Na or K, and R can be selected from Ca, Sr, Ba or Mg.

In the same way, it will be possible for the optical element according to the invention to be a calcium fluoride single crystal as well as a single crystal of NaF, of KF, of LiF, of $CaF_2$, of $BaF_2$, of $MgF_2$, or of $SrF_2$, or the mixed combinations of the latter fluorides, such as, for example, combinations of formulation $(M1)_x(M2)_{1-x}F_2$ in which M1 can be selected from Ba, Ca or Sr and x is such that $0 \leq x \leq 1$, or even combinations of formulation $Ca_{1-x-y}Ba_xSr_yF_2$ in which x and y are such that $0 \leq x \leq 1$ and $0 \leq y \leq 1$, or even combinations of formulation $MRF_3$ in which M can be selected from Li, Na or K, and R can be selected from Ca, Sr, Ba or Mg.

Even furthermore, it will be also possible for the method of the invention to be used for determining the optical quality of an optical fluoride crystal to be formed into a 100–200 nm wavelength optical element for use between 100 and 200 nm wavelengths.

When the fluoride single crystal is used as an optical element for applications other than projection systems in which a not as good optical quality is required, it will also be possible for the method of the invention to be applied for determining this lower optical quality.

This means that the invention comprises every technical equivalent of the means described, as well as the combinations thereof if these are done following its spirit.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. A method of making a below 200 nm wavelength fluoride crystal optical element, said method comprising:
    providing a fluoride single crystal,
    irradiating at least one volume element of the fluoride single crystal, along at least one family of crystalline planes with a hard x-ray beam, in order to obtain a picture of the diffraction in transmission mode of the hard x-rays across this at least one volume element along this at least one family of crystalline planes,
    studying the picture of the diffraction in transmission mode and calculating a mosaicity of the at least one volume element along the at least one family of crystalline planes to provide a selected optical fluoride crystal having a determined mosaicity of less than 10' across the at least one volume element,
    forming said selected optical fluoride crystal having a determined mosaicity of less than 10' across the at least one volume element into a below 200 nm wavelength fluoride crystal optical element having a mosaicity of less than 10'.

2. A method of making a below 200 nm wavelength fluoride crystal optical lithography projection element blank for forming into a below 200 nm wavelength fluoride crystal optical lithography projection element, said method comprising:
    providing a fluoride single crystal,
    irradiating at least one volume element of the fluoride single crystal, along at least one family of crystalline planes with a hard x-ray beam, in order to obtain a picture of the diffraction in transmission mode of the hard x-rays across this at least one volume element along this at least one family of crystalline planes,
    studying the picture of the diffraction in transmission mode and calculating a mosaicity of the at least one volume element along the at least one family of crystalline planes to provide a selected below 200 nm wavelength fluoride crystal optical lithography projection element crystal blank having a determined mosaicity of less than 10 across the at least one volume element.

3. A method of determining the optical quality of a below 200 nm wavelength fluoride single crystal, characterised in that it comprises the following steps:
    (a) irradiating at least one volume element of the fluoride single crystal, along at least one family of crystalline planes with a hard X-ray beam, in order to obtain a picture of the diffraction in transmission mode of the hard X-rays across this at least one volume element along this at least one family of crystalline planes,
    (b) studying the picture obtained in step (a), and
    (c) calculating the mosaicity of the at least one volume element along the at least one family of crystalline planes, from the study of step (b).

4. The method according to claim 3, characterised in that steps (a) to (c) are repeated along several families of crystalline planes in the at least one volume element.

5. The method according to claim 4, characterised in that the total mosaicity of the fluoride single crystal is calculated from the mosaicity calculations obtained in steps (c).

6. The method according to claim 3, characterised in that steps (a) to (c) are repeated in several different volume elements of the fluoride single crystal.

7. The method according to claim 3, characterised in that each volume element has a thickness, in the direction of the thickness of the fluoride single crystal, of 3 to 10 cm, and a surface area irradiated by the hard X-ray beam of 0.5 mm×20 to 40 mm.

8. The method according to claim 3, characterised in that the fluoride single crystals are selected having a mosaicity of less than 10' across the volume element(s).

9. The method according to claim 3, characterised in that the fluoride single crystal is a single crystal of NaF, of KF, of LiF, of $CaF_2$, of $BaF_2$, of $MgF_2$, or of $SrF_2$, or the mixed combinations of the latter fluorides, combinations of formulation $(M1)_x(M2)_{1-x}F_2$ in which M1 can be selected from Ba, Ca or Sr and x is such that $0 \leq x \leq 1$, or combinations of formulation $Ca_{1-x-y}Ba_xSr_yF_2$ in which x and y are such that $0 \leq x \leq 1$ and $0 \leq x \leq 1$, or combinations of formulation $MRF_3$ in which M can be selected from Li, Na or K, and R can be selected from Ca, Sr, Ba or Mg.

* * * * *